United States Patent [19]

Koshinaka et al.

[11] Patent Number: 5,030,842
[45] Date of Patent: Jul. 9, 1991

[54] FINE-PARTICLE MEASURING APPARATUS

[75] Inventors: Masao Koshinaka; Minoru Akiyama; Toshimasa Tomoda, all of Hyogo, Japan

[73] Assignee: Mitsubishi Denki Kabushiki Kaisha, Tokyo, Japan

[21] Appl. No.: 540,893

[22] Filed: Jun. 20, 1990

[30] Foreign Application Priority Data

Jun. 23, 1989 [JP] Japan .................................. 1-161234

[51] Int. Cl.$^5$ ............................................. G01N 21/86
[52] U.S. Cl. ..................................... 250/571; 356/237
[58] Field of Search ............... 250/571, 572, 574, 575, 250/237, 338; 356/339, 341, 343

[56] References Cited

U.S. PATENT DOCUMENTS

| | | | |
|---|---|---|---|
| 3,812,349 | 5/1974 | Gugliotta et al. | 356/237 |
| 4,049,352 | 9/1977 | Lardon et al. | 250/575 |
| 4,865,445 | 9/1989 | Kuriyama et al. | 356/237 |

FOREIGN PATENT DOCUMENTS 63-30570 6/1988 Japan .

OTHER PUBLICATIONS

Shintani et al., SiO$_2$ Particulates Dispersed in CVD Reactor, Electrochem. Soc.: Solid-State Science and Technology, Nov. 1977, pp. 1771-1776.

Primary Examiner—David C. Nelms
Assistant Examiner—Que Tan Le
Attorney, Agent, or Firm—Wolf, Greenfield & Sacks

[57] ABSTRACT

A fine-particle measuring apparatus designed to measure fine particles attached to the surface of a substrate of a semiconductor device set in a processing unit for formation of films, etching, cleaning, etc. and fine particles suspended in the space above the substrate surface by the use of scattering of a laser beam caused by these fine particles. The measuring apparatus comprises a laser light phase modulator for generating two laser beams which have the same wavelength and the phase difference between which is modulated at a predetermined frequency, an optical system which causes the two laser beams to intersect each other within a space containing the fine particles being the objects of measurement, a photodetector which receives light scattered by any of the fine particles in the region which the two laser beams intersect, and converts the received light into an electrical signal, and a signal processor which extracts from the electrical signal based on the scattered light of a signal component whose frequency is the same as or double that of a phase modulating signal for the modulation effected in the laser beam phase modulator and which has a constant phase difference with respect to the phase modulating signal. Thus, it is possible to measure fine particles with high spatial resolving power without substantially disturbing the environment inside the process unit or the process itself.

15 Claims, 5 Drawing Sheets

POSITION PERPENDICULAR TO INTERFERENCE FRINGES WITHIN REGION WHERE TWO LASER BEAMS INTERSECT

1

FINE-PARTICLE MEASURING APPARATUS

BACKGROUND OF THE INVENTION

1. Field of the Invention

The present invention relates to a fine-particle measuring apparatus for effecting measurement of fine particles (foreign matter) present in a process unit for formation of films, etching, cleaning, etc., for example, to a contamination inspection apparatus for detecting foreign matter on a wafer.

2. Description of the Prior Art

FIG. 3 shows the arrangement of a conventional fine particle measuring apparatus, as being a first prior art apparatus, disclosed, for example, in Japanese Patent Public Disclosure No. 63-30570 (1988). The apparatus is designed to measure fine particles attached to the surface of a wafer. In the figure, the reference numeral 1 denotes a substrate (wafer) for a semiconductor device which is an object of measurement, 2 a fine particle, 3 a laser light source (a light source for generating parallel rays), 4 a polarizer, 5 objective lenses, 6 a photodetector which converts light into an electrical signal, and 7 an electronic circuit device which processes information output from the photodetector 6 to obtain the results of measurement of fine particles. The reference numeral 8 denotes a driving mechanism for moving the position of the wafer 1.

The operation of the first prior art apparatus will next be explained. Laser light emitted from the laser light source 3 is applied almost parallel to the surface of the wafer 1. As the laser light that is applied to the wafer surface, for example, S-polarized laser light is employed. The S-polarized laser light is scattered by the fine particle 2. However, since the surface of the fine particle 2 has minute irregularities, the scattered light contains a large amount of P-polarized light. On the other hand, the medium constituting the measuring atmosphere is usually a gas, i.e., air, and light that is scattered by gas molecules in the manner of Rayleigh scattering contains no P-polarized light component. Accordingly, the scattered light caused by gas molecules is cut off by the polarizer 4 disposed in such a manner as to intercept the S-polarized light component. As a result, only the P-polarized light component of the scattered light from the fine particle 2 is received by the photodetector 6 through the objective lenses 5, and the result of measurement is obtained in the electronic circuit device 7. The driving mechanism 8 is provided to measure the distribution of fine particles on the wafer surface.

FIG. 4 is a sectional view showing the arrangement of another conventional fine-particle measuring apparatus, as being a second prior art apparatus, disclosed, for example, in A. Shintani et al.: J. Electrochem. Soc. 124, No. 11 (1977), p. 1771. In the figure, the reference numeral 3 denotes a laser light source, 9 an observation zone which is spatially limited by a light-receiving lens system 10 and which contains fine particles which are to be measured, 6 a photodetector, and 11 and optical trap for minimizing stray light in the measuring apparatus. In actual use, this prior art apparatus is connected to a process unit by the use of a capillary (tube) adapted to suck in a gas containing fine particles dispersed in the process unit, thereby indirectly measuring the fine particles in the process unit.

FIGS. 5(a) and 5(b) are plan and front views showing the operating principle of an in-situ particle flux monitor, as a third prior art apparatus.

Laser light from a laser 3 is reflected a large number of times between a pair of mirrors 21 disposed parallel to each other, thereby enlarging the two dimensional observation zone. When fine particles 2 are passing through the zone, light is scattered thereby and this scattered light is received by a photodetector 6 to thereby measure fine particles. It should be noted that the reference numeral 22 denotes reflecting condensers, while the numeral 23 denotes a beam stopper. This apparatus is used within a process unit.

The above-described prior arts suffer, however, from the following problems. In the fine-particle measuring apparatus according to the first prior art apparatus, it is necessary for a fine particle under measurement to have minute irregularities on its surface which are not much smaller in size than the wavelength of the laser light and, thus, it is difficult with this prior art apparatus to measure fine particles which have relatively smooth surfaces and fine particles which have relatively small particle diameters. These fine particles may be measured by the use of P-polarized laser light or non-polarized laser light in place of S-polarized laser light. In such a case, however, the Rayleigh-scattered light (P-polarized light) scattered by the gas that constitutes the measuring atmosphere cannot be cut off with the polarizer 4 and the S/N ratio cannot therefore be increased. Thus, it is difficult with the prior art apparatus to measure fine particles having small diameters. In addition, since this prior art apparatus is not adapted to measure fine particles in a process unit but is designed for off-line inspection, it is difficult to apply the prior art apparatus to the measurement of fine particles in a process unit even if the polarizer 4 and the objective lenses 5 (constituting in combination a microscope) are disposed in close proximity to the wafer 1 to limit the observation zone.

The fine-particle measuring apparatus according to the second prior art apparatus involves the problem that it is impossible to measure fine particles on the surface of a wafer set in the process unit and, with regard to the fine particles suspended in the process unit, it is only possible to measure those which can be successfully sucked and transported into the measuring apparatus.

The fine-particle measuring apparatus according to the third prior art apparatus is capable of measuring suspended fine particles but cannot measure those adhered to the wafer surface. In addition, since the optical system (comprising the laser light source 3, the mirrors 21, the photodetector 6, etc) is installed inside a process unit, in the case, for example, of a film forming process by atomspheric pressure thermal CVD, it is difficult to measure fine particles on the surface of a wafer heated to a high temperature or those which are suspended above the wafer surface during a film forming process. Even when no film is being formed, the presence of the apparatus also causes substantial changes in environment (e.g., the gas flow, temperature distribution, etc.) in the vicinity of the wafer. In an etching or cleaning process also, it is difficult to effect measurement without causing critical disturbances. In addition, since the measuring system according to this prior art apparatus has no means for eliminating signals (i.e., background noise) caused by light that is scattered by gas molecules constituting the measuring atmosphere medium in the manner of Rayleigh scattering, it is difficult to measure fine particles having such small particle diameters that the intensity of light scattered thereby is too weak to ensure that the desired signal will not be obscured by background noise.

SUMMARY OF THE INVENTION

In view of the above described problems of the prior arts, it is a primary object of the present invention to provide a fine-particle measuring apparatus which is capable of measuring with a high spatial resolving power fine particles adhered to the surface of a wafer set in a process unit for formation of films, etching, cleaning, etc. and as well as fine particles suspended in the space above the wafer surface without substantially disturbing the environment inside the process unit or the process itself.

To this end, the present invention provides a fine-particle measuring apparatus designed to measure fine particles adhered to the surface of a substrate for a semiconductor device and fine particles suspended in the space above the surface of the substrate by the use of scattering of a laser beam caused by these fine particles, comprising: a laser light phase modulator for generating two laser beams which have the same wavelength and the phase difference between which is modulated at a predetermined frequency; an optical system which causes the two laser beams to intersect each other within a space containing the fine particles as an object of measurement; a photodetector which receives light scattered by any of the fine particles in the region where the two laser beams intersect, and converts the received light into an electrical signal; and a signal processor which extracts from the electrical signal based on the scattered light a signal component whose frequency is the same as or double that of a phase modulating signal for the modulation effected in the laser beam phase modulator and which has a constant phase difference with respect to the phase modulating signal.

By virtue of the above-described arrangement, it is possible to eliminate from the measured signal and electrical signal component corresponding to stray light, that is, light other than the light resulting from the laser light. It is also possible to limit the measuring zone to the region where the two laser beams intersect each other and hence effect measurement with high S/N ratio and high spatial resolving power. Further, even in the limited measuring zone, the signal component corresponding to the Rayleigh-scattered light scattered by the atmosphere medium therein can be eliminated as long as the atmosphere medium in the measuring zone can be regarded as being homogeneous, so that it is possible to measure fine particles with high spatial resolving power while satisfactorily reducing causes of disturbance of the measurement.

In addition, if the intersection region of the two laser beams is moved within the process unit, it is possible to obtain the two-dimensional distribution of fine particles attached to the wafer surface and the three-dimentional distribution of fine particles suspended in the space above the wafer surface.

BRIEF DESCRIPTION OF THE DRAWINGS

The above and other objects, features and advantages of the present invention will become more apparent from the following description of the preferred embodiment thereof, taken in conjunction with the accompanying drawings, in which like reference numerals denote like elements, and of which.

DESCRIPTION OF THE PREFERRED EMBODIMENT

One embodiment of the present invention will be described below with reference to the accompanying drawings.

Figure 1:
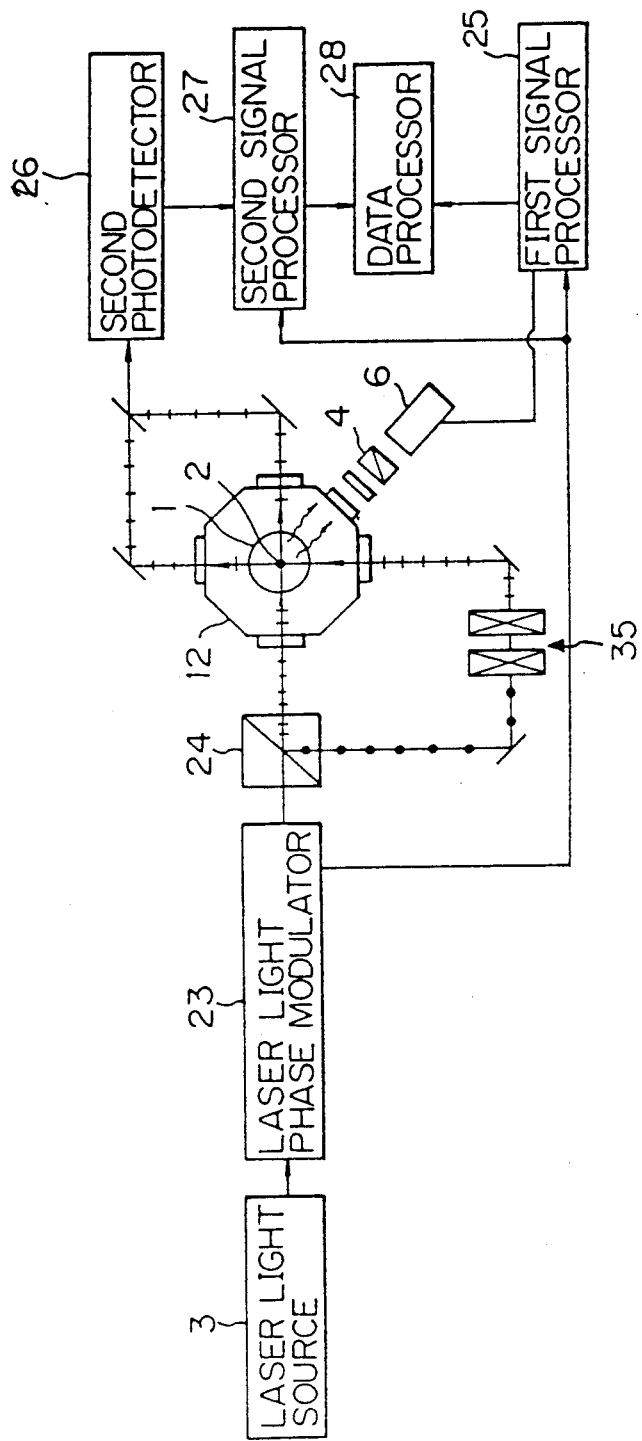
FIG. 1 shows the arrangement of one embodiment of the fine-particle measuring apparatus according to the present invention.

Referring to FIG. 1, the reference numeral 1 denotes a substrate (wafer) for a semiconductor device which is set in a process unit 12, 2 a fine particle attached to the surface of the wafer 1, 3 a laser light source, 23 a laser light phase modulator which provides a phase difference modulated at a predetermined frequency between the P-and S-polarized light components of laser light, 24 a polarization beam splitter which branches the laser light into two laser beams, that is, the P-polarized light component and the S-polarized light component, 4 a polarizer, 6 a first photodetector which receives through the polarizer 4 the laser light scattered by the fine particle 2 in the region where the two laser beams intersect, that is, the measuring zone, and converts it into an electrical signal, and 25 a first signal processor, for example, a lock-in amplifier, which extracts from an electrical signal output by the first photodetector 6 a signal component whose frequency is the same as or double that of the phase modulating signal employed in the laser light phase modulator 23 and which has a constant phase difference with respect to the phase modulating signal. The reference numeral 26 denotes a second photodetector, similar to the photodetector 6, which receives the resultant light from the two laser beams having passed through the process unit 12 and converts it into an electrical signal. The reference numeral 27 denotes a second signal processor, for example, a lock-in amplifier, similar to the first signal processor 25, which extracts from an electrical signal output by the second photodetector 26 a signal component whose frequency is the same as or double that of the phase modulating signal employed in the laser light phase modulator 23 and which has a constant phase difference with respect to the phase modulating signal.

It should be noted that the measuring section which mainly comprises the second photodetector 26 and the second signal processor 27 is adapted to monitor the operation of the fine-particle measuring apparatus according to the present invention. The reference numeral 28 denotes a data processor which obtains data concerning fine particles on the basis of the signal output from the first signal processor 25 and with the signal output from the second signal processor 27 being taken into consideration.

Furthermore, in FIG. 1, the reference numeral 35 denotes a pair of optical elements which cooperate to rotate a plane of polarization of an incident ray through an angle of 90°.

The laser light that is incident to the polarization beam splitter 24 is split into two beams which are in planes respectively perpendicular to each other. Since two laser light beams in perpendicular planes do not interfere with each other at all, it is necessary to align the polarization planes of two laser light beams to get them to interfere with each other. The polarization plane of one laser light beam is rotated through 90° by the optical elements 35 to thereby align the polarization planes of the two beams split by the splitter 24 with each other.

The operation of this embodiment will next be explained. Laser light emitted from the laser light source 3 is applied to the surface of the wafer 1 set in the process unit 12, or passes through the space above the surface of the wafer 1, after being branched off into two laser beams the phase difference between which is modulated at a predetermined frequency by the laser light phase modulator 23 and the polarization beam splitter 24. At this time, if the two laser beams are arranged to intersect each other on the surface of the wafer 1 or in the space above the wafer surface, interference fringes are formed in the intersection region of the two laser beams.

Figure 2A:
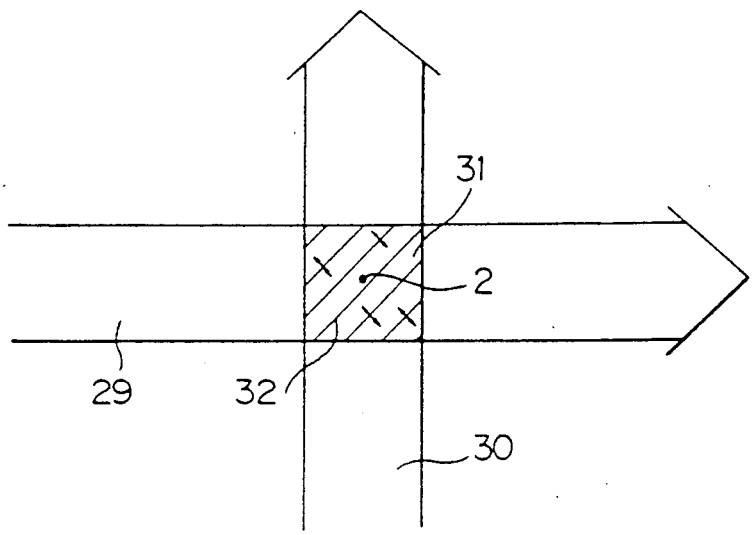
FIGS. 2(a) and 2(b) are views employed to explain the measuring principle of the present invention.
Figure 2B:
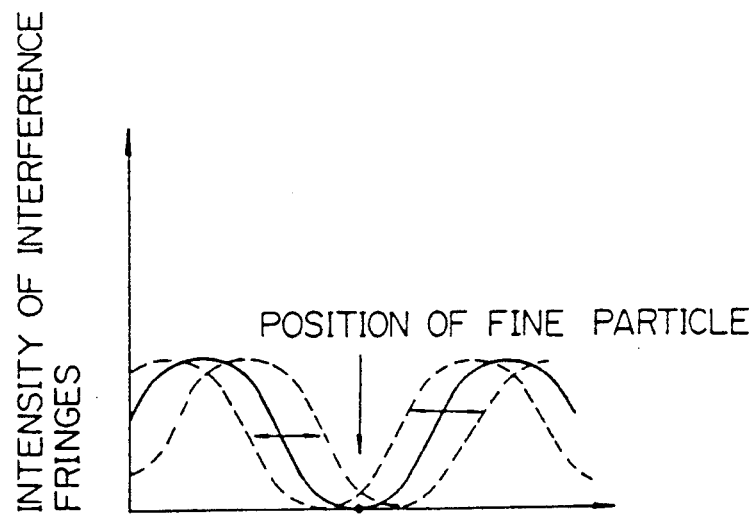
Figure 3:
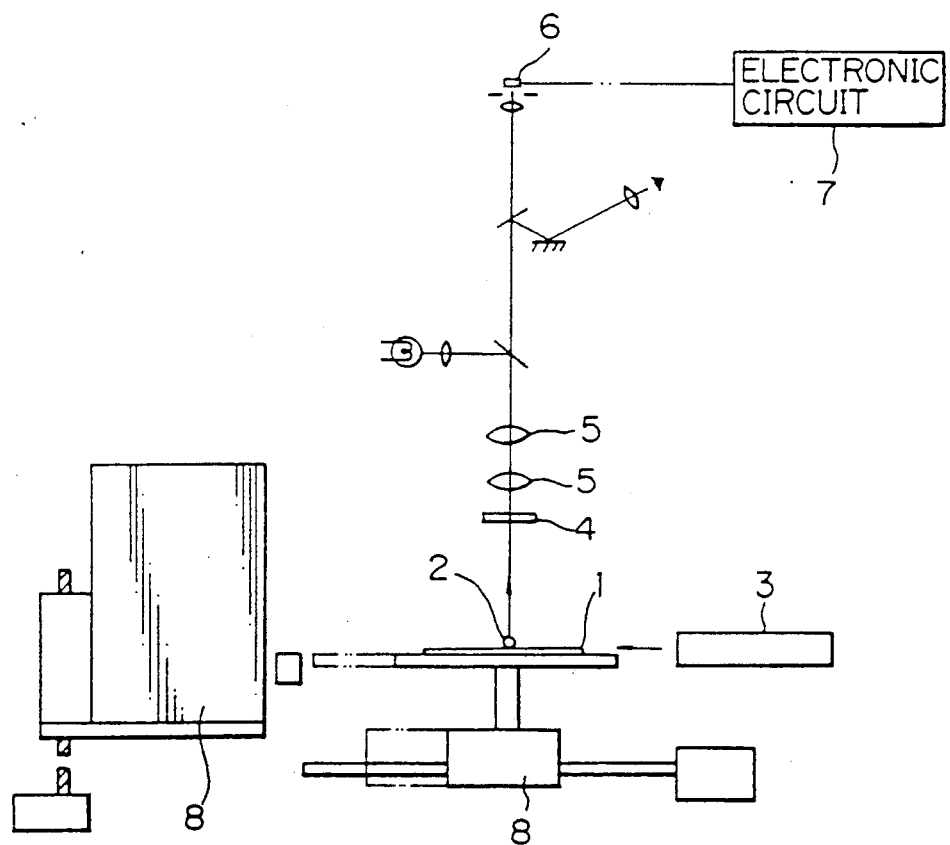
FIG. 3 is a schematic view showing the operating principle of a fine-particle measuring apparatus according to a first prior art.
Figure 4:
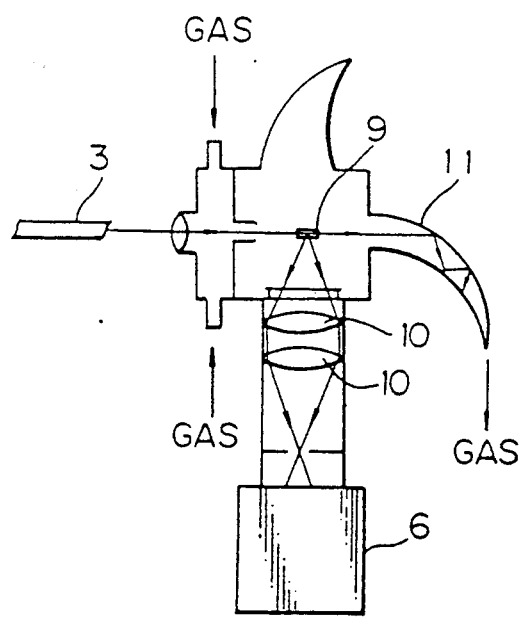
FIG. 4 is a sectional view showing the operating principle of a fine-particle measuring apparatus according to a second prior art.
Figure 5:
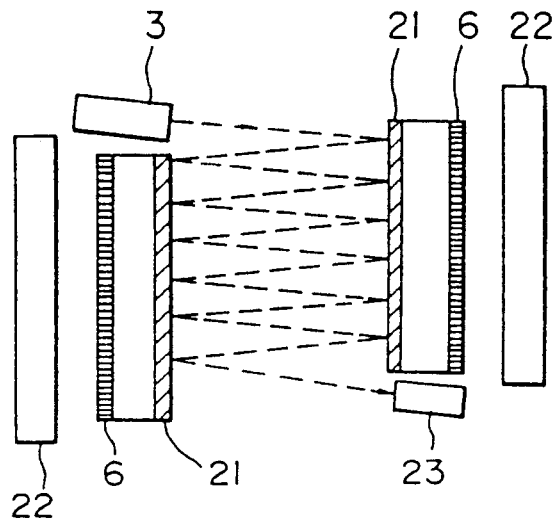
FIGS. 5(a) and 5(b) are plan and front views, respectively, of a fine particle measuring apparatus according to a third prior art, which show the operating principle of the apparatus.
Figure 5:
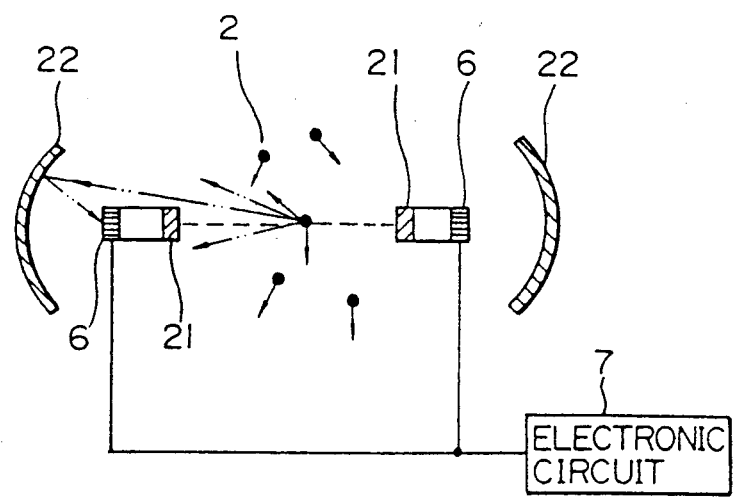

FIG. 2(a) shows the way in which interference fringes are formed in the intersection region of the two laser beams. In the figure, the reference numerals 29 and 30 denote two laser beams, respectively, 31 the region where the two laser beams 29 and 30 intersect, 32 interference fringes formed, and 2 a fine particle which is to be measured. Since the phase difference between the two laser beams 29 and 30 is modulated at a predetermined frequency, the interference fringes 32 move in synchronism with the modulation. Accordingly, the distribution of interference fringe intensities changes periodically at the position of the fine particle, as shown in FIG. 2(b), and consequently light that is scattered by the fine particle 2 is synchronous with the signal used to modulate the phase difference between the two laser beams 29 and 30. It is therefore possible to measure the fine particle 2 in the arrangement shown in FIG. 1 by converting the scattered light reflected by the fine particle 2 into an electrical signal in the first photodetector 6 and by extracting from the signal a signal component whose frequency is the same as or double that of the phase modulating signal employed in the laser light phase modulator 23 and which has a constant phase difference with respect to the phase modulating signal. Meantime, even if Rayleigh-scattered light scattered by the atmosphere medium that interferes with measurement of the fine particle 2 is present within the intersection region of the two laser beams, the signal component corresponding to the Rayleigh-scattered light can be eliminated as long as the atmosphere medium can be regarded as being homogeneous within the range where interference fringes move. It is therefore possible to measure fine particles having small diameters with a markedly high S/N ratio and high spatial resolving power in comparison with the prior art apparatus.

Although in the foregoing embodiment the present invention has been described by way of one example in which it is employed to measure fine particles in a process unit, the method that is used in the measuring apparatus of the present invention may, of course, be applied to a measuring apparatus which is designed to perform a measuring operation which is not related to a process unit and it may also effectively be applied to a contamination inspection apparatus for detecting foreign matter on the surface of a wafer.

Although in the foregoing embodiment the present invention has been described with regard to the measurement of fine particles 2 only in a limited region on the surface of the wafer 1 or within the space above the wafer surface, if the arrangement shown in FIG. 1 is provided with a mechanism which moves the intersection region of the two laser beams to a desired position with the process unit 12, it is possible to readily measure the two-dimentional distribution of fine particles attached to the surface of the wafer 1 and the three-dimensional distribution of fine particles suspended in the space above the wafer surface.

In addition, although in the arrangement shown in FIG. 1 the laser light is branched off into two laser beams by the polarization beam splitter 24 after the phase difference between the P-and S-polarized components of the laser light has been modulated in the laser light phase modulator 23 in order to generate two laser beams which have the same wavelength and the phase difference between which is modulated at a predetermined frequency, the arrangement may be such that the laser beam is first branched off into two laser beams and then one laser beam is subjected to phase modulation; in such a case also, the same advantageous effects as those described above are obtained, as a matter of course.

As has been described above, the fine-particle measuring apparatus according to the present invention comprises a laser light phase modulator for generating two laser beams which have the same wavelength and the phase difference between which is modulated at a predetermined frequency, an optical system which causes the two laser beams to intersect each other within a space containing fine particles being the objects of measurement, a photodetector which receives light scattered by any of the fine particles in the region where the two laser beams intersect, and converts the received light into an electrical signal, and a signal processor which extracts from the electrical signal based on the scattered light a signal component whose frequency is the same as or double that of a phase modulating signal for the modulation effected in the laser beam phase modulator and which has a constant phase difference with respect to the phase modulating signal. It is therefore possible to measure with high S/N ratio and high spatial resolving power fine particles attached to the surface of a substrate for a semiconductor device which is set in a process unit and fine particles suspended in the space above the substrate surface without substantially disturbing the environment inside the process unit and the process itself. Moreover, it is possible to accurately measure fine particles having smaller diameters than in the case of the prior art apparatus.

Although the present invention has been described through specific terms, it should be noted here that the described embodiment is not necessarily exclusive and that various changes and modifications may be imparted thereto without departing from the scope of the invention which is limited solely by the appended claims.

What is claimed:

1. A fine-particle measuring apparatus designed to measure fine particles attached to the surface of a substrate of a semiconductor device and fine particles suspended in the space above the surface of said substrate by the use of scattering of a laser beam caused by these fine particles, comprising:
- a laser light phase modulator for generating two laser beams which have the same wavelength and the phase difference between which is modulated at a predetermined frequency;
- an optical system which causes said two laser beams to intersect each other within a space containing said fine particles being the objects of measurement;
- a photodetector which receives light scattered by any of said fine particles in the region where said two laser beams intersect, and converts the received light into an electrical signal; and
- a signal processor which extracts from the electrical signal based on the scattered light a signal component whose frequency is the same as or double that of a phase modulating signal for said modulation effected in said laser beam phase modulator and which has a constant phase difference with respect to said phase modulating signal.

2. A fine-particle measuring apparatus as set forth in claim 1 includinq a polarization beam splitter coupled from said modulator for providing said laser beams.

3. A fine-particle measuring apparatus as set forth in claim 2 includinq a polarizer coupled between said space and said photodetector.

4. A fine-particle measuring apparatus as set forth in claim 1 includinq a second photodetector for receiving the resultant light from the two laser beams after having passed through said space.

5. A fine-particle measuring apparatus as set forth in claim 4 including a second signal processor which extracts from an electrical signal output by the second photodetector, a signal component whose frequency is the same as or double that of the phase modulating signal employed in the laser light phase modulator and which has a constant phase difference with respect to the phase modulating signal.

6. A fine-particle measuring apparatus as set forth in claim 1 includinq a polarization beam splitter coupled from said modulator for providing said laser beams, and optical element means for rotating the plane of polarization of one of said beams.

7. A fine-particle measuring apparatus as set forth in claim 1 wherein said optical system includes a pair of optical elements which cooperate to rotate a plane of polarization of one of said laser beams.

8. A fine-particle measuring apparatus designed to measure fine particles by the use of scatting of a laser beam caused by these fine particles, comprising:
- means for establishing two laser beams which have the same wavelength and a phase difference therebetween which is modulated at a predetermined frequency:
- an optical system which causes said two laser beams to intersect each other within a space containing said fine particles that are to be measured;
- at least a first photodetector which receives light scattered by any of said fine particles in the region where said two laser beams intersect, and converts the received light into an electrical signal; and
- at least a first signal processor which extracts from the electrical signal based on the scattered light a signal component whose frequency is the same as or double that of the phase modulating signal and which has a constant phase difference with respect to said phase modulating signal.

9. A fine-particle measuring apparatus as set forth in claim 8 wherein said means for establishing two laser beams comprises a laser light phase modulator.

10. A fine-particle measuring apparatus as set forth in claim 9 further including a polarization beam splitter coupled from said modulator for providing said laser beams.

11. A fine-particle measuring apparatus as set forth in claim 10 including a polarizer coupled between said space and said photodetector.

12. A fine-particle measuring apparatus as set forth in claim 8 including a second photodetector for receiving the resultant light from the two last beams after having passed through said space.

13. A fine-particle measuring apparatus as set forth in claim 12 including a second signal processor which extracts from an electrical signal output by the second photodetector, a signal component whose frequency is the same as or double that of the phase modulating signal and which has a constant phase difference with respect to the phase modulating signal.

14. A fine-particle measuring apparatus as set forth in claim 8 includinq a polarization beam splitter coupled from said modulator for providing said laser beams, and optical element means for rotating the plane of polarization of one of said beams.

15. A fine-particle measuring apparatus as set forth in claim 8 wherein said optical system includes a pair of optical elements which cooperate to rotate a plane of polarization of one of said laser beams.

* * * * *